(12) United States Patent
Ueno

(10) Patent No.: US 6,956,056 B2
(45) Date of Patent: *Oct. 18, 2005

(54) METHOD FOR PROVIDING A CATHARTIC EFFECT

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/147,980

(22) Filed: May 20, 2002

(65) Prior Publication Data

US 2003/0022933 A1 Jan. 30, 2003

Related U.S. Application Data

(60) Provisional application No. 60/291,635, filed on May 18, 2001.

(51) Int. Cl.[7] ............... A61K 31/5575; C07C 405/00
(52) U.S. Cl. ............... 514/530; 514/573; 560/121; 562/503
(58) Field of Search .............. 560/121; 562/503; 514/530, 573

(56) References Cited

U.S. PATENT DOCUMENTS

| | | |
|---|---|---|
| 3,969,376 A | 7/1976 | Magerlein |
| 3,969,379 A | 7/1976 | Magerlein |
| 3,969,381 A | 7/1976 | Magerlein |
| 5,164,415 A | 11/1992 | Ueno |
| 6,242,485 B1 * | 6/2001 | Ueno .................. 514/530 |
| 2003/0130352 A1 * | 7/2003 | Ueno et al. .................. 514/573 |

FOREIGN PATENT DOCUMENTS

| | | |
|---|---|---|
| DE | 3404209 A | 9/1984 |
| EP | 0153858 | 9/1985 |
| EP | 0310305 A | 4/1989 |
| EP | 0857718 A | 8/1998 |
| GB | 1396206 A | 6/1975 |
| GB | 1436831 A | 5/1976 |
| JP | 2-32055 A | 2/1990 |

OTHER PUBLICATIONS

Clark et al., Current Opinion in Endocrinology & Diabetes (1994), 1st Ed., pp. 56–59.*

English translation Office Action—Patent Rejection Decision letter from the Intellectual Property Office, Aug. 1, 2003.

B. S. Tsai, et al. Preferential Binding of the Novel Prostaglandin SC 46275 to Canine Gastric Versus Intestinal Receptors[1].

* cited by examiner

*Primary Examiner*—Laura L. Stockton
(74) *Attorney, Agent, or Firm*—Sughrue Mion, PLLC

(57) ABSTRACT

The present invention relates to a novel method for providing a cathartic effect to a patient in need of cathartic induction, which comprises administering to the patient a cathartic-inducing effective amount of halogenated bioactive lipid comprising the following partial structure (I):

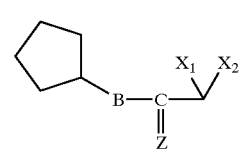

(I)

The method is useful for relieving or preventing constipation, and also for cleansing the gastrointestinal tract.

9 Claims, 1 Drawing Sheet

METHOD FOR PROVIDING A CATHARTIC EFFECT

CROSS REFERENCE TO RELATED APPLICATION

This application claims benefit from U.S. Provisional Application 60/291,635, filed May 18, 2001; the disclosure of which is incorporated herein by reference.

TECHNICAL FIELD

The present invention relates to a novel method for providing a cathartic effect. The method is useful for relieving or preventing constipation, and also for cleansing the gastrointestinal tract.

ART RELATED

Constipation is classified into a functional constipation such as atonic constipation, spastic constipation and rectal constipation, an organic constipation caused by a bowel disease and a stenosis due to postoperative adhesion and the like, and a drug-induced constipation.

Cathartics conventionally used for relieving these constipating conditions include, for example, 1) large bowel-stimulant anthraquinone cathartics, 2) small bowel-stimulant castor oil, 3) bulking cathartics such as carboxymethyl cellulose, 4) salt cathartics such as magnesium sulfate and 5) saccharide cathartics such as sugar alcohol. However, these cathartics work by forcible activation due to stimulating the bowel, so that they bring diarrhea like feces and induce side effects such as stomachache when evacuating.

Gastrointestinal cleansing by means of promoting bowel movement has been employed in preparation for endoscopic examination, diagnostic or surgical procedures such as colonoscopy, barium enema X-rays and intravenous pyelography, and emergency procedures such as emergency gastrointestinal flush for poison removal.

Electrolyte cleansing method has been generally used for cleansing the bowel, which comprises inducing diarrhea by ingesting a large volume of isotonic water containing electrolytes only. However, because of the ingestion of a large volume of water, the method could not be used for patients with nephropathy, cardiac disorder or hypertension. Recently, PEG/electrolyte cleansing composition consisting of sodium sulfate, potassium chloride, sodium chloride, sodium bicarbonate and water binding polyethylene glycol (PEG), which was reported by Davis et al. in 1980, is most frequently used. However, this PEG/electrolyte cleansing composition usually requires ingestion of a large volume of solution as large as 2–4 liters, and it is hard to take because of its salty, oily and slimy tastes. For these reasons, it takes a long time and gives considerable pains to take the required volume. Accordingly, it has been desired to develop a drug that is easy to take and has a desirable effect in a smaller volume.

Meanwhile, bioactive lipids, for example, arachidonic acid metabolites, platelet-activating factor, lysophosphatidic acid, lipid-soluble vitamin, endotoxin and the like, are deeply involved in regulating differentiation and proliferation of cells, biophylaxis and nerve function. The bioactive lipids derived from arachidonic acid include, for example, prostaglandins and thromboxane.

Prostaglandins (hereinafter, referred to as PG(s)) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

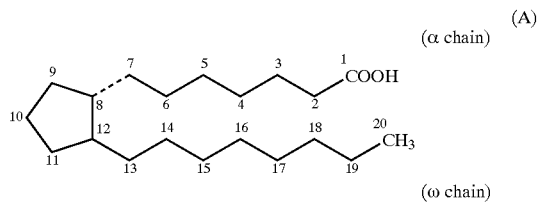

On the other hand, some of synthetic analogues of primary PGs have modified skeletons. The primary PGs are classified to PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:

Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a β-configuration).

PGs are known to have various pharmacological and biological activities. For example, PGs induce vasodilation, inflammation and platelet agglutination; stimulate uterine and intestinal tract; and also exhibit anti ulcer action. Further, PGEs or PGFs stimulate intestinal tract and strongly contradict the tract, but they exert only poor enteropooling effects. Because of side effects such as stomachache due to the intestinal tract contraction, PGEs or PGFs cannot be used as cathartics.

SUMMARY OF THE INVENTION

The present invention relates to a novel cathartic composition that is useful for relieving or preventing constipation, and also for cleansing the gastrointestinal tract.

The present invention also relates to a method for relieving or preventing constipation as well as a method for cleansing the gastrointestinal tract.

The present inventor has conducted pharmacological investigations on the bioactive lipids, and found that halogenated bioactive lipid having at least the following partial structure exerts a remarkable cathartic action, which has resulted in the completion of the present invention.

Namely, the present invention relates to a method for providing a cathartic effect to a patient in need of cathartic induction, which comprises administering to the patient a cathartic-inducing effective amount of halogenated bioactive lipid comprising the following partial structure (I):

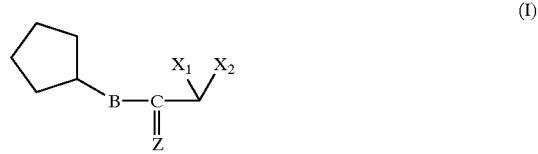

wherein B is —$CH_2$—$CH_2$—, —CH=CH— or —C≡C—;

Z is

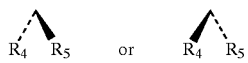

wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$X_1$ and $X_2$ are hydrogen, lower alkyl or halogen, and at least one of them is halogen.

Especially the present invention relates to a method for providing a cathartic effect to a patient in need of cathartic induction, which comprises administering to the patient a cathartic-inducing effective amount of halogenated bioactive lipid represented by the formula (II):

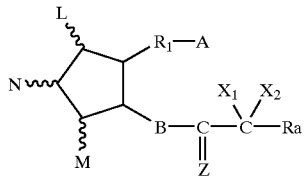

(II)

wherein L, M and N are hydrogen, hydroxy, halogen, lower alkyl, hydroxy(lower)alkyl or oxo, wherein at least one of L and M is a group other than hydrogen, and the five-membered ring may have at least one double bond;

A is —$CH_2OH$, —$COCH_2OH$, —COOH or a functional derivative thereof;

B is —$CH_2$—$CH_2$—, —CH=CH— or —C≡C—;

Z is

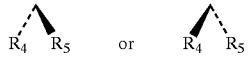

wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$R_1$ is a saturated or unsaturated bivalent lower or medium aliphatic hydrocarbon residue, which is unsubstituted or substituted with halogen, alkyl, hydroxy, oxo, aryl or heterocyclic group and at least one of carbon atoms in the aliphatic hydrocarbon is optionally substituted by oxygen, nitrogen or sulfur;

$X_1$ and $X_2$ are hydrogen, lower alkyl or halogen, and at least one of them is halogen; and Ra is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic or hetrocyclic-oxy group; cyclo(lower)alkyl; cyclo(lower)alkyloxy; aryl; aryloxy; heterocyclic or heterocyclic-oxy group.

In another aspect, the present invention relates to a cathartic composition comprising a cathartic effective amount of halogenated bioactive lipid comprising the above partial structure (I).

Especially, the present invention also relates to a cathartic composition comprising a cathartic effective amount of halogenated bioactive lipid represented by the above formula (II).

DETAILED DESCRIPTION OF THE INVENTION

Figure 1:
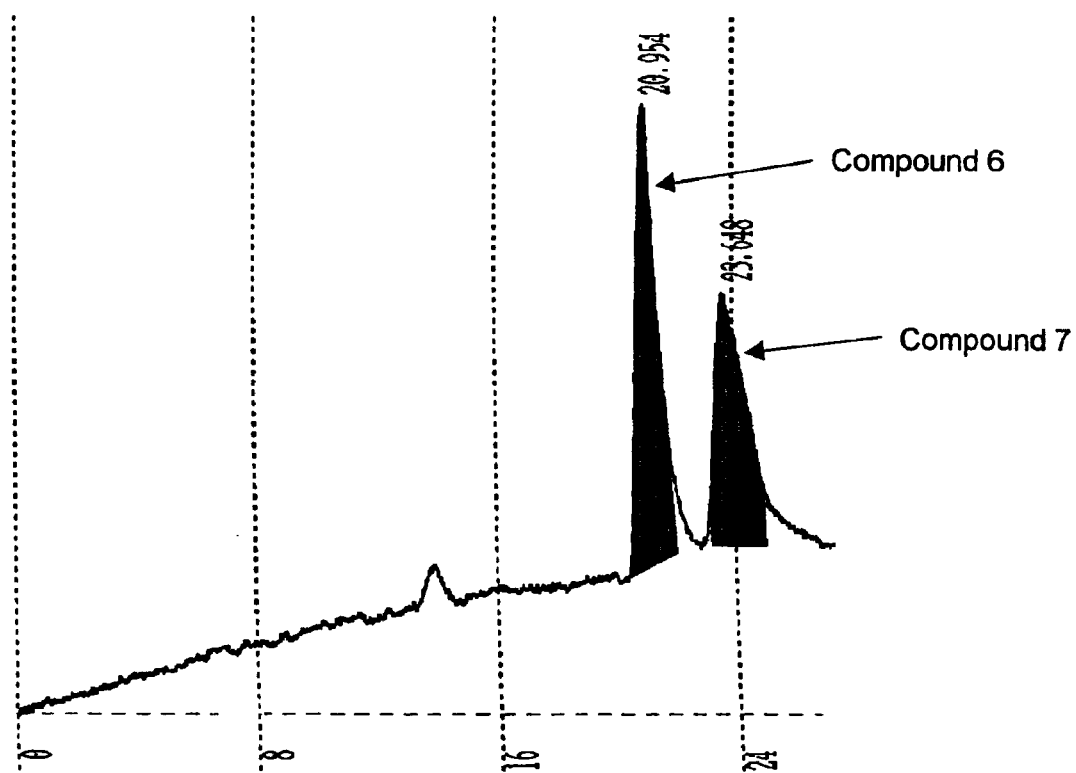
FIG. 1 represents HPLC pattern of compound 5. The compound was resolved into epimers (compounds 6 and 7).

The nomenclature of the PG compounds, which are one of the bioactive lipids, used herein is based on the numbering system of prostanoic acid represented in the above formula (A).

The formula (A) shows a basic skeleton of the C-20 carbon atoms, but the present invention is not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification, these terms also include those having substituents other than the hydroxy group at positions 9 and/or 11. Such compounds are referred to as 9-dehydroxy- 9-substituted-PG compounds or 11-dehydroxy-11-substituted-PG compounds. A PG compound having hydrogen in place of the hydroxy group is simply named as 9- or 11-dehydroxy compound.

As stated above, the nomenclature of the prostaglandin compounds is based on the prostanoic acid skeleton. However, in case the compound has a similar partial structure as a prostaglandin, the abbreviation of "PG" may be used. Thus, a PG compound of which α-chain is extended by two carbon atoms, that is, having 9 carbon atoms in the α-chain is named as 2-decarboxy-2-(2-carboxyethyl)-PG compound. Similarly, a PG compound having 11 carbon atoms in the α-chain is named as 2-decarboxy-2-(4-carboxybutyl)-PG compound. Further, a PG compound of which ω-chain is extended by two carbon atoms, that is, having 10 carbon atoms in the ω-chain is named as 20-ethyl-PG compound. These compounds, however, may also be named according to the IUPAC nomenclatures.

The PG compound used in the present invention may include any PG derivatives or analogs insofar as having a hydroxy group at 15 position and at least one halogen atom at 16 position. Accordingly, for example, a PG type 1 compound having a double bond at 13–14 position, a PG type 2 compound having two double bond at 13–14 and 5–6 position, a PG type 3 compound having three double bond at 5–6, 13–14 and 17–18 position, 13,14-dihydro-PG compound wherein the double bond at 13–14 position is single bond.

Typical examples of the compounds used in the present invention include PG type 1, PG type 2, PG type 3, 13,14-dihydro-PG type 1, 13,14-dihydro-PG type 2, 13,14-dihydro-PG type 3 and the derivatives or analogs thereof.

Examples of the analogs (including substituted derivatives) or derivatives include a PG compound of which carboxy group at the end of α-chain is esterified; a compound of which α-chain is extended; physiologically acceptable salt thereof; a compound having a double bond at 2–3 position or a triple bond at position 5–6, a compound having substituent(s) at position 3, 5, 6, 16, 17, 18, 19 and/or 20; and a compound having lower alkyl or a hydroxy (lower) alkyl group at position 9 and/or 11 in place of the hydroxy group.

According to the present invention, preferred substituents at position 3, 17, 18 and/or 19 include alkyl having 1–4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. According to the invention, at least one of substituents at position 16 is substituted by halogen atom. Preferred substituents at position 17 include lower alkyl such as methyl and ethyl, hydroxy, halogen atoms such as chlorine and fluorine, and aryloxy such as trifluoromethylphenoxy. Preferred substituents at position 20 include saturated or unsaturated lower alkyl such as C1–4 alkyl, lower alkoxy such as C1–4 alkoxy, and lower alkoxy alkyl such as C1–4 alkoxy-C1–4 alkyl. Preferred substituents at position 5 include halogen atoms such as chlorine and fluorine. Preferred substituents at position 6 include an oxo group forming a carbonyl group. Stereochemistry of PGs having hydroxy, lower alkyl or hydroxy(lower)alkyl substituent at position 9 and/or 11 may be α, β or a mixture thereof.

Further, the above derivatives and analogs may be compounds having an alkoxy, cycloalkyl, cycloalkyloxy, phenoxy or phenyl group at the end of the ω-chain where the chain is shorter than the primary PGs.

An especially preferred compound used in the present invention is represented by the formula (III):

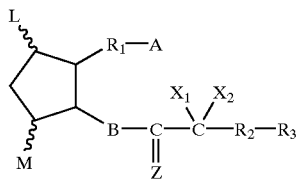

(III)

wherein L and M are hydrogen, hydroxy, halogen, lower alkyl, hydroxy(lower)alkyl or oxo, wherein at least one of L and M is a group other than hydrogen, and the five-membered ring may have at least one double bond;
A is —CH$_2$OH, —COCH$_2$OH, —COOH or a functional derivative thereof;
B is —CH$_2$—CH$_2$—, —CH=CH— or —C≡C—;
Z is

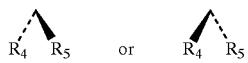

wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;
R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atoms in the aliphatic hydrocarbon is optionally substituted by oxygen, nitrogen or sulfur;
X$_1$ and X$_2$ are hydrogen, lower alkyl or halogen, and at least one of them is halogen;
R$_2$ is a single bond or lower alkylene; and
R$_3$ is lower alkyl, lower alkoxy, cyclo(lower)alkyl, cyclo(lower)alkyloxy, aryl, aryloxy, heterocyclic group or heterocyclic-oxy group.

Especially the compound of formula (II), wherein B is —CH$_2$—CH$_2$— and X$_1$ and X$_2$ are same or different halogen atoms, that is, the compound represented by formula (IV):

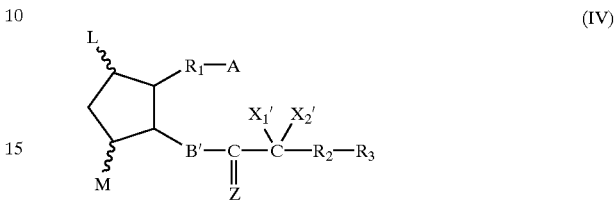

(IV)

wherein L and M are hydrogen, hydroxy, halogen, lower alkyl, hydroxy(lower)alkyl or oxo, wherein at least one of L and M is a group other than hydrogen, and the five-membered ring may have at least one double bond;
A is —CH$_2$OH, —COCH$_2$OH, —COOH or a functional derivative thereof;
B' is —CH$_2$—CH$_2$—;
Z is

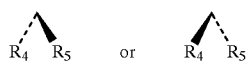

wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;
R$_1$ is a saturated or unsaturated bivalent lower or medium aliphatic hydrocarbon residue, which is unsubstituted or substituted with halogen, alkyl, hydroxy, oxo, aryl or heterocyclic group and at least one of carbon atoms in the aliphatic hydrocarbon is optionally substituted by oxygen, nitrogen or sulfur;
X$_1$' and X$_2$' are same or different halogen atoms;
R$_2$ is a single bond or lower alkylene; and
R$_3$ is lower alkyl, lower alkoxy, cyclo(lower)alkyl, cyclo(lower)alkyloxy, aryl, aryloxy, heterocyclic group or heterocyclic-oxy group is novel and preferred according to the present invention, and covered by the scope of the present invention.

In the above formula, the term "unsaturated" in the definitions for R$_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alky" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cycio(lower)alkyl—O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tri-cyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl- monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower)alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A means a group represented by the formula —CONR'R", wherein each of R' and R" is hydrogen atom, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonyl-amide and tolylsulfonylamide.

Preferred examples of L and M include hydroxy and oxo, and especially, M is hydroxy and L is oxo which has a 5-membered ring structure of, so called, PGE type.

Preferred A is —COOH, its pharmaceutically acceptable salt, ester or amide thereof.

Preferred B is —CH$_2$—CH$_2$—, which provides so-called 13,14-dihydro type compound.

Preferred X$_1$ and X$_2$, or X$_1$' and X$_2$' are fluorine atoms, which provide so called 16,16-difluoro type compound.

Preferred R1 is a hydrocarbon residue containing 1–10 carbon atoms, preferably 6–10 carbon atoms, further at least one of carbon atoms in the aliphatic hydrocarbon is optionally substituted by oxygen, nitrogen or sulfur.

Examples of R$_1$ may include the following groups:

—CH$_2$—CH$_2$—CH$_2$—CH$_2$—CH$_2$—CH$_2$—,
—CH$_2$—CH═CH—CH$_2$—CH$_2$—CH$_2$—,
—CH$_2$—CH$_2$—CH$_2$—CH$_2$—CH═CH—,
—CH$_2$—C≡C—CH$_2$—CH$_2$—CH$_2$—,
—CH$_2$—CH$_2$—CH$_2$—CH$_2$—CH (CH$_3$)—CH$_2$—,
—CH$_2$—CH$_2$—CH$_2$—CH$_2$—O—CH$_2$—,

—CH$_2$—CH=CH—CH$_2$—O—CH$_2$—,
—CH$_2$—C≡C—CH$_2$—O—CH$_2$—,
—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—,
—CH$_2$—CH$_2$—CH$_2$—CH$_2$—CH$_2$—CH=CH—,
—CH$_2$—C≡C—CH$_2$—CH$_2$—CH$_2$—CH$_2$—,
—CH$_2$—CH$_2$—CH$_2$—CH$_2$—CH$_2$—CH(CH$_3$)—CH$_2$—,
—CH$_2$—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—CH$_2$—,
—CH$_2$—CH$_2$—CH$_2$—CH$_2$—CH$_2$—CH$_2$—CH=CH—,
—CH$_2$—C≡C—CH$_2$—CH$_2$—CH$_2$—CH$_2$—CH$_2$—,
—CH$_2$—CH$_2$—CH$_2$—CH$_2$—CH$_2$—CH$_2$—CH(CH$_3$)—CH$_2$—.

Preferred Ra is a hydrocarbon containing 1–10 carbon atoms, more preferably, 1–8 carbon atoms. Ra may have one or two side chains having one carbon atom.

The configuration of the ring and the α- and/or ω chains in the above formula (II), (III) and (IV) may be the same as or different from that of the primary PGs. The present invention also includes a mixture of a compound having a primary type configuration and a compound of a non-primary type configuration.

The typical example of the present compound is 13,14-dihydro-16-mono or difluoro-PGE compound and the derivative or analogue thereof.

In the present invention, any of isomers such as the individual tautomeric isomers, the mixture thereof, or optical isomers, the mixture thereof, a racemic mixture, and other steric isomers may be used for the same purpose.

According to the present invention, the subject to be treated by the invention may be any mammalian subject including human beings.

According to the present invention, the cathartic-inducing effective amount may vary depending on the strain of animal or human, age, body weight, symptom of the subject to be treated, desired therapeutic effect, administration route, term of treatment and the like. Typically, systemic administration of 0.00001–100 mg/kg per day by administering 1–4 times per day or continuous administration may provide a satisfactory effect.

According to the present invention, the method may be carried out with the composition of the present invention. The composition can be applied systemically or topically. Usually, the composition is administered by oral administration, intravenous injection (including infusion), subcutaneous injection, intra rectal administration, intra vaginal administration and the like.

The cathartic composition of the present invention may be formulated as a composition for oral administration, for injection, for instillation or for external administration, tablet, sublingual, suppository and vaginal suppository.

The composition of the present invention may further contain physiologically acceptable additives. Said additives may include conventional ingredients used with a bioactive lipid such as excipient, diluent, filler, resolvent, lubricant, adjuvant, binder, disintegrator, coating agent, cupsulating agent, ointment base, suppository base, aerozoling agent, emulsifier, dispersing agent, suspending agent, thickener, tonicity agent, buffering agent, soothing agent, preservative, antioxidant, corrigent, flavor, colorant, a functional material such as cyclodextrin and biodegradable polymer. The additives may be selected depending on the dosage form from those described in general reference books of pharmaceutics.

The amount of the compound having the partial structure of formula (I) in the present composition may vary depending on the dosage form of the composition, and may generally be 0.0001–10.0 wt %, more preferably 0.001–1.0 wt %.

Examples of solid compositions for oral administration include tablets, troches, sublingual tablets, capsules, pills, powders, granules and the like. The solid composition may be prepared by mixing one or more active ingredients with at least one inactive diluent. The composition may further contain additives other than the inactive diluents, for example, a lubricant, a disintegrator and a stabilizer. Tablets and pills may be coated with an enteric or gastroenteric film, if necessary. The composition may be covered with two or more layers. The composition may also be adsorbed to a sustained release material, or microcapsulated. Additionally, the composition may be capsulated by means of an easily degradable material such as gelatin. The solid composition may be dissolved in an appropriate solvent such as fatty acid or its mono, di or triglyceride to provide a soft capsule. Sublingual tablets may be prepared to provide a composition with fast-acting property.

Examples of liquid compositions for oral administration include emulsions, solutions, suspensions, syrups and elixirs and the like. Said composition may further contain conventionally used inactive diluents, e.g., purified water and ethyl alcohol. The composition may contain additives other than the inactive diluents such as adjuvant, e.g., wetting agents and suspending agents, sweeteners, flavors, fragrances and preservatives.

The composition of the present invention may be in the form of spraying composition, which contains one or more active ingredients and may be prepared according to a known method.

Examples of injectable compositions of the present invention for parenteral administration include sterile aqueous or nonaqueous solutions, suspensions and emulsions. Diluents for the aqueous solution or suspension may include, for example, distilled water of injection grade, physiological saline and Ringer's solution. Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radiation sterilization. The injectable composition may also be provided as a sterilized powder composition to be dissolved in an injection-grade sterilized solvent before use.

Another form of the composition of the present invention is suppository or pessary, which may be prepared by mixing the active ingredients into a base such as cacao butter that softens at body temperature, and nonionic surfactants having suitable softening temperatures may be used to improve absorbability.

The term "treatment" used herein includes any means of control such as prevention, care, relief of the condition, attenuation of the condition and arrest of progression.

The compound of the invention exhibits a remarkable enteropooling effect, and also remarkably accelerates intestinal transportability. In fact, because of the remarkable cathartic effect on animals and human beings, the composition of the present invention is effective for relieving or preventing constipation, and also for cleansing the gastrointestinal tract.

Included in the types of constipation to be treated, although not particularly limited, are functional constipation such as relaxing constipation, spastic constipation and rectal constipation; organic constipation caused by intestinal diseases and stenosis due to postoperative adhesion; and constipation induced by a drug such as opioid. Further, because of speedy recovery from diarrhea symptoms, the present compound is useful as a cathartic composition such as a laxative and a drastic purgative.

In addition to relieving or preventing constipation, the present composition may be used for preventing a patient with hernia or cardiovascular diseases from straining at stool, or for softening feces of a patient with anorectal diseases. Moreover, the present composition may be used for cleansing the gastrointestinal tract in preparation for endoscopic examination or for diagnostic or surgical procedures such as colonoscopy, barium enema X-rays and intravenous pyelography, and emergency procedures such as emergency gastrointestinal flush for poison removal and the like.

The present invention will be described in more detail with reference to the following examples, which is not intended to limit the scope of the present invention.

SYNTHESIS EXAMPLE (1) t-butyldimethylsilylation of the Compound 1

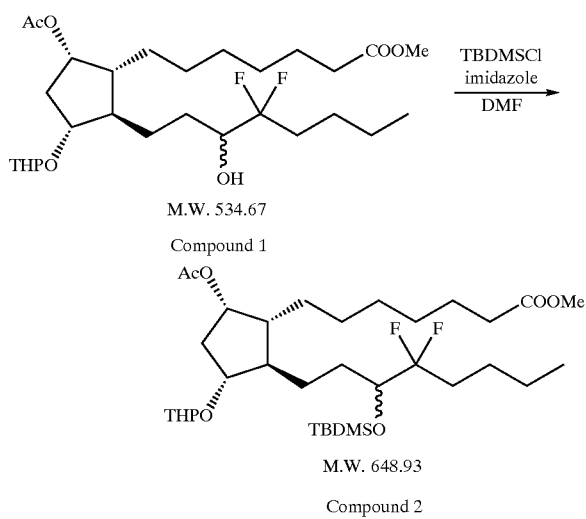

After dissolving 180 mg (0.337 mmol) of the compound 1 in anhydrous DMF 0.38 mL, imidazole 100.8 mg (1.481 mmol) was added thereto. Next, t-butyldimethylsilyl chloride 111.7 mg (0.741 mmol) was added to the solution and agitated for three hours at room temperature and then for 14.5 hours at 37° C. Saturated aqueous ammonium chloride 0.5 mL was added to the reaction and then, the reaction mixture was extracted with ethyl acetate 5 mL for three times. Organic layers were combined, washed with saturated saline 5 mL and dried with anhydrous magnesium sulfate. After vacuum concentration, the residue was purified with silica gel column. [Fuji Silysia Chemical BW-300 20 g, developer: ethyl acetate/n-hexane=1/3→1/1] Yield: 145.3 mg; 66%; colorless oil $^1$H-NNR spectrum (200 MHz/CDCl$_3$) of the compound 2 δ: 5.11–5.01 (m, 1H), 4.63–4.51 (m, 1H), 4.00–3.60 (m, 3H), 3.∂(s, 3H), 3.56–3.40 (m, 1H), 2.40–2.10 (m, 1H), 2.30 (t, J=7.4 Hz, 2H), 2.04 (s, 3H), 2.00–1.08 (m, 29H), 0.99–0.85 (m, 12H), 0.08 (s, 6H)

(2) Hydrolysis of the Compound 2

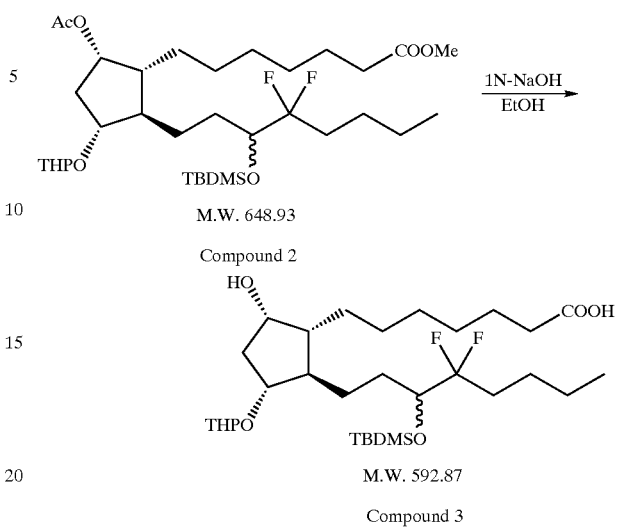

After dissolving 145.3 mg (0.224 mmol) of the compound 2 in ethanol 6.3 mL, 1N-sodium hydroxide 0.67 mL (0.67 mmol) was added thereto and agitated for three hours at room temperature. Then 1N-sodium hydroxide 0.45 mL (0.45 mmol) was added to the solution and agitated for 16 hours at room temperature. Water 1 mL was added to the solution, which was acidified (pH4) with 1N-hydrochloric acid 0.79 mL. After that, saturated saline 1.5 mL was added to the solution, and then, the reaction mixture was extracted with ethyl acetate 10 mL for three times. Organic layers were combined and dried with anhydrous magnesium sulfate. After vacuum concentration, the residue was purified with silica gel column. [Fuji Silysia Chemical FL-60D (water content 15%) 7 g, developer: ethyl acetate] Yield: 130.6 mg; 98%; pale yellow oil $^1$H-NNR spectrum (200 MHz/CD$_3$OD) of the compound 3 δ: 4.76–4.60 (m, 1H), 4.23–3.65 (m, 6H), 3.65–3.23 (m, 1H), 2.40–1.05 (m, 32H), 1.03–0.90 (m, 12H), 0.20–0.03 (m, 6H)

(3) Dess-Martin Oxidization of the Compound 3

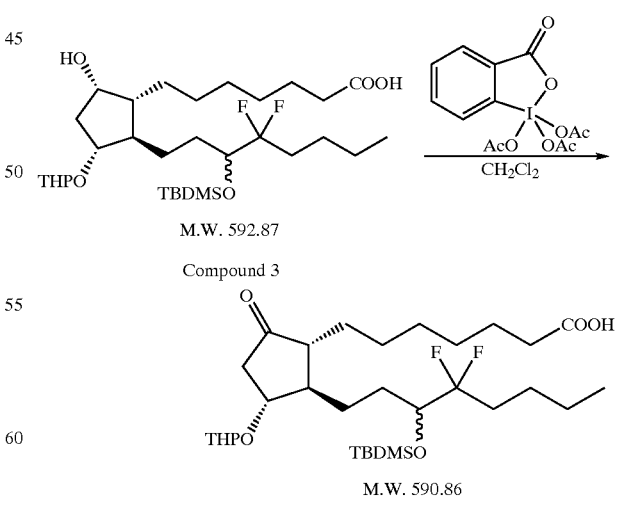

Under argon atmosphere, after dissolving 41.5 mg (0.07 mmol) of the compound 3 in anhydrous dichloromethane 0.56 mL, Dess-Martin reagent 118.8 mg (0.28 mmol) was added thereto and agitated for one hour at room temperature. Monitoring reaction status with TLC showed that the reaction was not entirely completed. Then Dess-Martin reagent 59.4 mg (0.14 mmol) and anhydrous dichloromethane 0.2 mL were added to the solution and agitated for 2.5 hours at room temperature. Again, Dess-Martin reagent 59.4 mg (0.14 mmol) and anhydrous dichloromethane 0.7 mL were added to the solution and agitated for 2.5 hours at room temperature. Additionally, Dess-Martin reagent 89.1 mg (0.21 mmol) and anhydrous dichloromethane 0.7 mL were added to the solution and agitated for 13 hours at room temperature. Saturated aqueous sodium thiosulfate 20 mL was added to the solution and agitated for three minutes, and then, the reaction mixture was extracted with ethyl acetate 40 mL twice. Organic layers were combined, washed with saturated sodium bicarbonate solution 8 mL and saturated saline 8 mL and dried with anhydrous magnesium sulfate. After vacuum concentration, the residue was purified with silica gel column. [Fuji Silysia Chemical FL-60D (water content 15%) 7 g, developer: ethyl acetate/n-hexane=1/2→ ethyl acetate]

Yield: 37.9 mg; 92%; pale yellow oil $^1$H-NNR spectrum (200 MHz/CDCl$_3$) of the compound 4
δ: 4.73–4.60 (m, 1H), 4.16 (q, J=7.0 Hz 3/5H), 4.00–3.61 (m, 12/5H), 3.61–3.43 (m, 1H), 2.83–2.60 (m, 4/5H), 2.43–1.05 (m, 146/5H), 2.35 (t, J=7.2 Hz, 2H), 1.00–0.83 (m, 12H), 0.09 (m, 6H)

(4) Detetrahydropyranylation and de-t-butylmethyl Silylation of the Compound 4

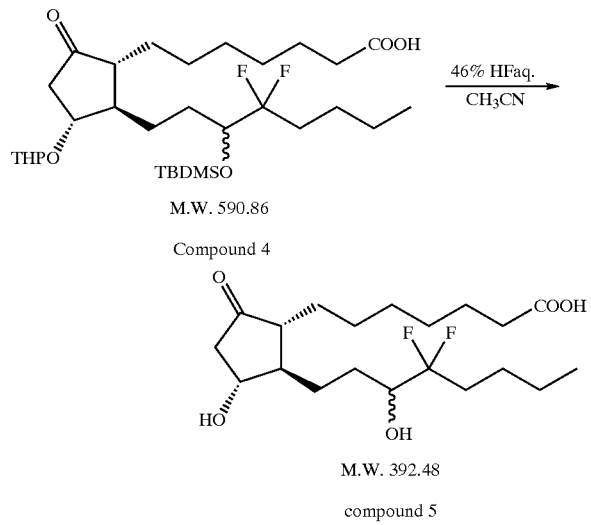

Compound 4

M.W. 392.48 compound 5

After dissolving 37.9 mg (0.0∝mmol) of the compound 4 in acetonitrile 3.26 mL and cooling it down to 0° C., hydrofluoric acid/acetonitrile mixed solution (3.26 mL, acetonitrile: 46% hydrofluoric acid=10:1) was added thereto and agitated for three hours at 0° C. Monitoring reaction status with TLC showed that the reaction was not entirely completed. Then the reaction solution was stood still in the refrigerator for 15 hours. Even after that, the reaction was not entirely completed. Then the reaction solution was agitated for three hours at 10° C.–13° C. and further agitated for two hours at 23° C. After neutralizing (pH4) the solution with saturated sodium bicarbonate solution, saturated saline 1 mL was added thereto and then the reaction mixture with ethyl acetate 25 mL three times. Organic layers were combined, washed with saturated saline 1 mL and dried with anhydrous magnesium sulfate. After vacuum concentration, the residue was purified with silica gel column to obtain the compound 5. [Fuji Silysia Chemical FL-60D (water content 15%) 5 g, developer: ethyl acetate/ n-hexane=1/1→3/2→7/3→4/1]

Yield: 4.4 mg; 17.5%; colorless oil $^1$H-NNR spectrum (200 MHz/CDCl$_3$) of the compound 5
δ: 4.25–4.08 (1H, m, 11-H), 3.88–3.64 (1H, m, 15-H), 2.83–2.60 (1H, m, 10-H$_\beta$), 2.35 (2H, t, J=7.2 Hz, 2-H$_2$), 2.31–2.10 (1H, m, 10-H$_\alpha$), 2.10–1.20 (22H, m, 3-H$_2$, 4-H$_2$, 5-H$_2$, 6-H$_2$, 7-H$_2$, 8-H, 12-H, 13-H$_2$, 14-H$_2$, 17-H$_2$, 18-H$_2$, 19-H$_2$), 0.93 (3H, t, J=7.1 Hz, CH$_3$)

(5) Resolution of Compound 5 into Epimers 64.5 mg of the compound 5 was fractionated by HPLC according to the following condition.

| [Fractional condition] | |
|---|---|
| Column: | Merck Hibar Lichrosorb DIOL (7 μm) 25 × 250 mm (Lot. 600008) |
| Mobile phase: | Hexane/IPA = 90/10 |
| Elution mode: | Isocratic |
| Detection: | UV-294 nm |
| Flow rate: | 30 mL/min |
| Injection amount: | ca. 30 mg (2 mL inj.)/shot |

24 mg of the crude compound 6 (recovery 46%, colorless oil) and 19 mg of the crude compound 7 (recovery 36.5%, colorless oil) were obtained.

The crude compound 6 was purified with silica gel column again [Fuji Silysia Chemical BW-300 5.2 g, developer: ethyl acetate/n-hexane=1/1→3/2→7/3→4/1→5/1]. 19 mg of the purified compound 6 (recovery 79%, colorless oil) was obtained.

The crude compound 7 was purified with HPLC again. 15.4 mg of the purified compound 7(recovery 81%, colorless oil) was obtained.

$^1$H-NNR spectrum (200 MHz/CDCl$_3$) of the compound 6
δ: 4.23–4.09 (1H, m, 11-H), 3.84–3.63 (1H, m, 15-H), 2.73 (1H, dd, J=18.2, 7.0 Hz, 10-H$_\beta$), 2.35 (2H, t, J=7.2 Hz, 2-H$_2$), 2.25 (1H, dd, J=18.4, 7.8 Hz, 10-H$_\alpha$), 2.20–1.20 (22H, m, 3-H$_2$, 4-H$_2$, 5-H$_2$, 6-H$_2$, 7-H$_2$, 8-H, 12-H, 13-H$_2$, 14-H$_2$, 17-H$_2$, 18-H$_2$, 19-H$_2$), 0.94 (3H, t, J=7.2 Hz, CH$_3$)

$^1$H-NNR spectrum (200 MHz/CDCl$_3$) of the compound 7
δ: 4.25–4.09 (1H, m, 11-H), 3.88–3.65 (1H, m, 15-H), 2.72 (1H, dd, J=18.3, 6.8 Hz, 10-H$_\beta$), 2.35 (2H, t, J=7.2 Hz, 2-H$_2$), 2.23 (1H, dd, J=18.5, 7.5 Hz, 10-H$_\alpha$), 2.13–1.20 (22H, m, 3-H$_2$, 4-H$_2$, 5-H$_2$, 6-H$_2$, 7-H$_2$, 8-H, 12-H, 13-H$_2$, 14-H$_2$, 17-H$_2$, 18-H$_2$, 19-H$_2$), 0.93 (3H, t, J=7.1 Hz, CH$_3$)

Test Example (Enteropooling Effect)

Male Wistar rats (Crj Wistar Rat, body weight: 180–200 g) were used. Animals were fasted for 24 hours with free access to water. 5 mL/kg of distilled water containing the compound 5, PGE$_1$ or PGE$_2$ was orally administrated (p.o.), or 2 mL/kg of physiological saline containing the compound 5 was injected intravenously (i.v.) to the animals. Thirty minutes after the administration, the animals were euthanized by cervical dislocation, and the abdominal cavity was opened surgically. The intestinal fluid was collected and its volume was measured. The dose of test substance yielding a 50% increase in intestinal fluid volume relative to the control group, which was received the vehicle only, was defined as the ED$_{50}$ value. Results are shown in Table 1.

TABLE 1

| Test substance | Administration route | Enteropooling $ED_{50}$ µg/kg |
|---|---|---|
| Compound 5 | p.o. | 0.6 |
| Compound 5 | i.v. | 0.88 |
| $PGE_1$ | p.o. | 420 |
| $PGE_2$ | p.o. | 130 |

Compound 5: 13,14-dihydro-15RS-hydroxy-16,16-difluoro-PGE1

The above result indicates that the present compound has a significant enteropooling effect.

What is claimed is:

1. A method for the treatment of constipation or for cleansing the gastrointestinal tract, which comprises administering to the patient a cathartic-inducing effective amount of a halogenated bioactive lipid compound represented by the formula (II):

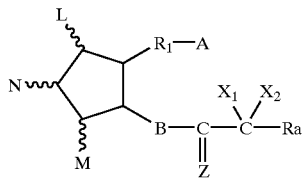

(II)

wherein L, M and N are hydrogen, hydroxy, halogen, lower alkyl, hydroxy(lower)alkyl or oxo, wherein at least one of L and M is a group other than hydrogen, and the five-membered ring may have at least one double bond;

A is —$CH_2$—OH, —$COCH_2OH$, —COOH or a salt, an ether, an ester or an amide thereof;

B is —$CH_2$—$CH_2$—, —CH=CH— or —C≡C—;

Z is

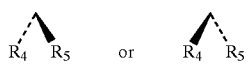

wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$R_1$ is a saturated or unsaturated bivalent lower or medium aliphatic hydrocarbon residue, which is unsubstituted or substituted with halogen, alkyl, hydroxy, oxo, aryl or heterocyclic group and at least one of carbon atoms in the aliphatic hydrocarbon is optionally substituted by oxygen, nitrogen or sulfur;

$X_1$ and $X_2$ are hydrogen, lower alkyl or halogen, and at least one of them is halogen;

and

Ra is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic or heterocyclic-oxy group; cyclo(lower)alkyl; cyclo(lower)alkyloxy; aryl; aryloxy; heterocyclic or heterocyclic-oxy group.

2. The method as described in claim 1, wherein said compound is 16-mono or dihalogen-prostaglandin compound.

3. The method as described in claim 1, wherein said compound is 13,14-dihydro-16-mono or dihalogen-prostaglandin compound.

4. The method as described in claim 1, wherein said compound is 16-mono or difluoro-prostaglandin compound.

5. The method as described in claim 1, wherein said compound is 13,14-dihydro-16-mono or difluoro-prostaglandin compound.

6. The method as described in claim 1, wherein said compound is 16-mono or dihalogen-prostaglandin E compound.

7. The method as described in claim 1, wherein said compound is 13,14-dihydro-16,16-difluoro-prostaglandin $E_1$.

8. The method as described in claim 1, which is for treating constipation.

9. The method as described in claim 1, which is for cleansing the gastrointestinal tract.

* * * * *